(12) United States Patent
Goldman

(10) Patent No.: US 11,064,709 B2
(45) Date of Patent: **\*Jul. 20, 2021**

(54) CONTROLLED ENVIRONMENT SHIPPING CONTAINERS

(71) Applicant: Australis Aquaculture, LLC, Greenfield, MA (US)

(72) Inventor: Joshua N. Goldman, Montague, MA (US)

(73) Assignee: AUSTRALIS AQUACULTURE, LLC, Greenfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/933,602

(22) Filed: Jul. 20, 2020

(65) Prior Publication Data

US 2021/0000128 A1 Jan. 7, 2021

Related U.S. Application Data

(63) Continuation of application No. 16/580,613, filed on Sep. 24, 2019, now Pat. No. 10,750,754, which is a
(Continued)

(51) Int. Cl.
*A23B 7/148* (2006.01)
*G01N 33/00* (2006.01)
*A23L 3/3418* (2006.01)

(52) U.S. Cl.
CPC ............ *A23B 7/148* (2013.01); *A23L 3/3418* (2013.01); *G01N 33/0036* (2013.01)

(58) Field of Classification Search
CPC ............ G01N 33/0004; G01N 33/0036; A23B 7/144; A23B 7/148; A23B 7/152;
(Continued)

(56) References Cited

U.S. PATENT DOCUMENTS 3,365,307 A 1/1968 Dixon
5,156,009 A 10/1992 Woodruff
(Continued)

FOREIGN PATENT DOCUMENTS

FR 2868254 10/2005
GB 1132151 10/1968
(Continued)

OTHER PUBLICATIONS

International Search Report and Written Opinion of PCT-US2015-027317 titled "Controlled Environment Shipping Containers" dated Aug. 10, 2015.
(Continued)

*Primary Examiner* — Benjamin R Schmitt
(74) *Attorney, Agent, or Firm* — Hamilton, Brook, Smith & Reynolds, P.C.

(57) ABSTRACT

Systems and apparatus are provided for maintaining an ultra low oxygen concentration in a shipping container for the purpose of preventing spoilage of perishable food products. The system and apparatus may contain a composition of a mixture of gases including one or more of nitrogen, carbon dioxide, and another inert gas, wherein the mixture of gases positively pressurizes the shipping container with an ultra low oxygen concentration. The system and apparatus may use one or more sensors to monitor the composition of the mixture of gases, and may use one or more controllers to release the compressed gases into the interior of the container. The controller may release the compressed gases at a variable rate of release sufficient to maintain the ultra low oxygen concentration and to ensure consistent concentrations of the mixture of gases with the container.

20 Claims, 4 Drawing Sheets

Related U.S. Application Data continuation of application No. 14/694,674, filed on Apr. 23, 2015, now Pat. No. 10,426,177.

(60) Provisional application No. 61/986,210, filed on Apr. 30, 2014.

(58) Field of Classification Search
CPC .. A23L 3/3409; A23L 3/34095; A23L 3/3418; A23L 3/3445
See application file for complete search history.

(56) References Cited

U.S. PATENT DOCUMENTS

| | | | |
|---|---|---|---|
| 5,623,105 A | 4/1997 | Liston et al. | |
| 5,649,995 A | 7/1997 | Gast, Jr. | |
| 5,801,317 A | 9/1998 | Liston et al. | |
| 5,872,721 A | 2/1999 | Huston et al. | |
| 6,179,986 B1 | 1/2001 | Swette et al. | |
| 6,615,908 B1 | 9/2003 | Bosher et al. | |
| 7,765,733 B1 | 8/2010 | Liu | |
| 10,426,177 B2 | 10/2019 | Goldman | |
| 10,750,754 B2 | 8/2020 | Goldman | |
| 2006/0199267 A1 | 9/2006 | Savur et al. | |
| 2007/0065546 A1 | 3/2007 | Jorgensen et al. | |
| 2012/0325086 A1 | 12/2012 | Schaefer | |
| 2013/0013099 A1 | 1/2013 | Delele et al. | |

FOREIGN PATENT DOCUMENTS

| | | |
|---|---|---|
| JP | 2008050027 | 3/2008 |
| WO | WO 2015-167930 | 11/2015 |

OTHER PUBLICATIONS

International Preliminary Report on Patentability for PCT-US2015-027317 dated Nov. 1, 2016, titled "Controlled Environment Shipping Containers".

Notice of Allowance and Fee(s) Due for U.S. Appl. No. 16/580,613, titled "Controlled Environment Shipping Containers," dated Jul. 22, 2020.

FIG. 1B

Apparatus 200

Sensor 250

Controller 240

Cartons with Perishable Food Products 260

Source of Compressed Inert Gas 230

Shipping Container 210

Composition of a Mixture of Gases 220

FIG. 2

CONTROLLED ENVIRONMENT SHIPPING CONTAINERS

RELATED APPLICATIONS

This application is a continuation of U.S. application Ser. No. 16/580,613, filed Sep. 24, 2019, which is a continuation of U.S. application Ser. No. 14/694,674, filed Apr. 23, 2015, now U.S. Pat. No. 10,426,177, issued Oct. 1, 2019, which claims the benefit of U.S. Provisional Application No. 61/986,210, filed on Apr. 30, 2014. This application is also related to PCT Application No. PCT/US2015/027317, filed on Apr. 23, 2015. The entire teachings of the above applications are incorporated herein by reference.

BACKGROUND

In a normal atmospheric environment, the storage life of perishable food products is limited. Traditional modified atmosphere packaging replaces the normal atmospheric environment before storage or shipment, but the environment is not modified over time. The traditional modified atmosphere packaging has limitations stemming from no atmosphere modification after sealing until delivery. This can result in premature product spoilage caused by unacceptably high oxygen concentrations due to emissions from the product or interior packaging components, the permeability of the packaging materials or a broken seal. Some prior art modified atmosphere shipping containers rely on gas permeable membranes to regulate the gas composition within a container by molecular separation. Other prior art containers rely on a reactive fuel cell using a chemical process to remove oxygen. The limitations of the current modified atmosphere shipping systems include their high cost, operational complexity, the inability to optimize the ratio of inert gasses, and the limited rate of gas treatment or discharge. These limitations are addressed by the inventions described herein.

SUMMARY

Embodiments of the present invention provide a controlled environment system, device, and apparatus that maintain a low oxygen concentration to slow the rate of spoilage of perishable food products. For example, the controlled environment apparatus releases stored gases to maintain an ultra low oxygen concentration environment to prevent spoilage of perishable food products.

In some embodiments, the system or apparatus for maintaining an ultra low oxygen concentration may comprise a shipping container that includes a plurality of walls. The system or apparatus may contain a composition of a mixture of gases including one or more of nitrogen, carbon dioxide, and another inert gas, wherein the mixture of gases positively pressurizes the shipping container and has an ultra low oxygen concentration. In some embodiments, at least one source of a compressed or liquid nitrogen, a carbon dioxide, and an inert gas may be used to maintain the composition of the mixture of gases. The system or apparatus may use one or more sensors to monitor the composition of the mixture of gases. The system or apparatus may also use one or more controllers to release the compressed gases into the interior of the container, wherein a variable rate of release is sufficient to maintain the ultra low oxygen concentration and to ensure consistent concentrations of the mixture of gases within the container. The system or apparatus may maintain the ultra low oxygen concentration for the purpose of preventing spoilage of perishable food products.

In some embodiments, the shipping container is a standard or Controlled Atmosphere ("CA") refrigerated shipping container.

In some embodiments, the ultra low oxygen concentration is less than about 6,000 ppm. In other embodiments, the ultra low oxygen concentration may be less than 4,000 ppm or less than 2,000 ppm.

In some embodiments, the composition of the mixture of gases includes carbon dioxide. In these and other embodiments, the composition of the mixture of gases may include nitrogen or one or more inert gasses, such as argon, krypton and helium.

In some embodiments, one sensor monitors oxygen concentration. In these and other embodiments, other sensors may monitor other gas concentrations, rate of use of the stored compressed gases, and temperature in the container.

In some embodiments, the controller may integrate predictive algorithms to regulate the rate of release of the stored compressed gas. In embodiments, the controller may regulate release of the gas at a rate which anticipates leakage or other sources of contribution of oxygen. In other embodiments, the controller may be coupled to an oxygen sensor to minimize or shut off stored compressed gas release when the oxygen level is at or below a minimum set point.

In some embodiments, the one or more sensors maintain an electronic record, such as a log, of one or more of a temperature, the gas mixture concentrations, and the rate of use of the stored gas.

In some embodiments, a power supply may be linked to container or be independent of container.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1B is a block diagram of certain components of the computer nodes in the network of FIG. 1A.

FIG. 2 shows a schematic of a system or apparatus comprising a plurality of cartons in an embodiment.

DETAILED DESCRIPTION

A description of example embodiments of the invention follows.

Digital Processing Environment

Figure 1A:
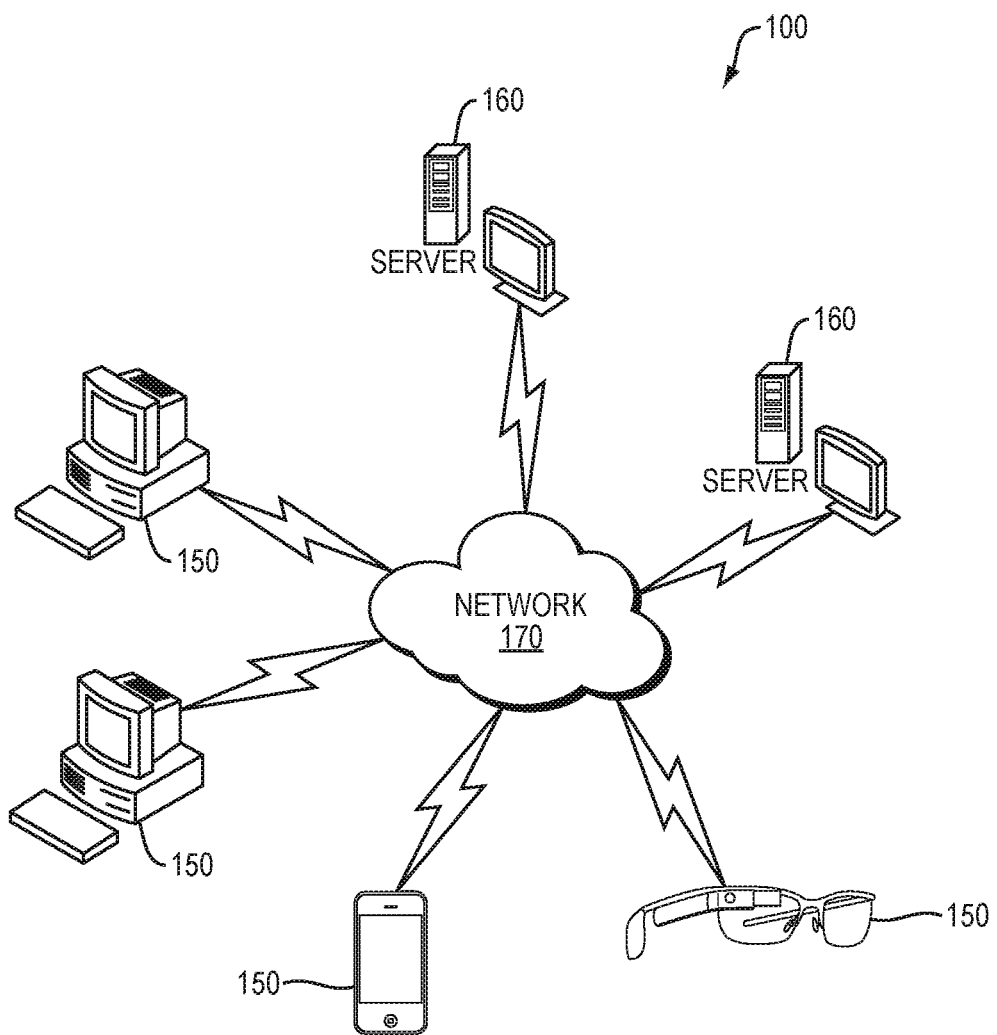
FIG. 1A is a schematic diagram of an example computer network environment in which embodiments of the invention are deployed.

Example implementations of controllers to release the compressed gases into the interior of the controlled environment shipping containers may be implemented in a software, firmware, or hardware environment. FIG. 1A illustrates one such example digital processing environment in which embodiments of the present invention may be implemented. Client computers/devices 150 and server computer/devices 160 (or a cloud network 170) provide processing, storage, and input/output devices executing application programs and the like.

Client computers/devices 150 may be linked directly or through communications network 170 to other computing devices, including other client computers/devices 150 and server computer/devices 160. The communication network 170 can be part of a wireless or wired network, remote access network, a global network (i.e. Internet), a worldwide collection of computers, local area or wide area networks, and gateways, routers, and switches that currently use a variety of protocols (e.g. TCP/IP, Bluetooth®, RTM, etc.) to communicate with one another. The communication network 170 may take a variety of forms, including, but not limited to, a data network, voice network (e.g. land-line, mobile, etc.), audio network, video network, satellite network, radio network, and pager network. Other electronic device/computer networks architectures are also suitable.

Client computers/devices 150 may be sensors, such as gas and temperature sensors, that monitor and log conditions in the shipping container. Server computers 160 may be controllers configured to provide a controlled environment system 100 which communicates with client devices 150, such as the gas and temperature sensors, for controlling the release of compressed gases into the interior of the shipping containers. The server computers may not be separate server computers but part of cloud network 170. In some embodiments, a server computer (controller) may operate locally within the shipping container. In these embodiment and other embodiments, the controller may be an industrial programmable logic controller (PLC), or other such controller configured with firmware similar to PLC firmware. The sensors 150 may communicate information regarding the conditions of a shipping container, such as the gas concentrations or temperature, to the controllers 160. In some embodiments, the sensors 150 may include client applications executing on the sensors 150 for monitoring and logging the conditions, and communicating the information regarding the conditions to the controllers 160. Client computers/devices 150 may also be devices to configure the sensors 150 and controllers 160, such as configuring the gas concentration thresholds for releasing compressed gases into the interior of the shipping container.

Figure 1B:
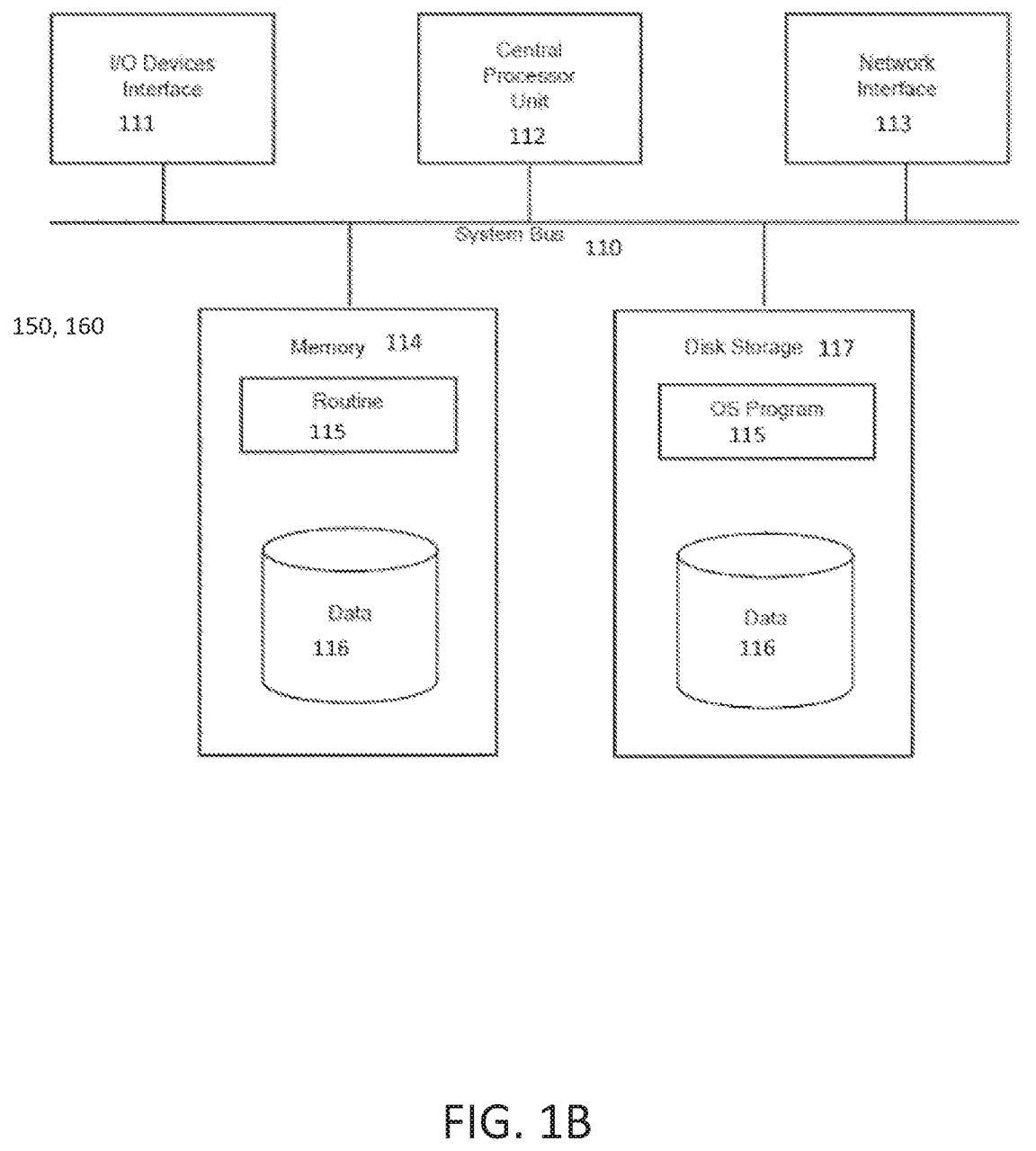

FIG. 1B is a block diagram of any internal structure of a computer/computing node (e.g., client processor/device 150 or server computers 160) in the processing environment of FIG. 1A, which may be used to facilitate processing audio, image, video or data signal information. Each computer 150, 160 in FIG. 1B contains a system bus 110, where a bus is a set of actual or virtual hardware lines used for data transfer among the components of a computer or processing system. The system bus 110 is essentially a shared conduit that connects different elements of a computer system (e.g., processor, disk storage, memory, input/output ports, etc.) that enables the transfer of data between elements.

Attached to the system bus 110 is an I/O device interface 111 for connecting various input and output devices (e.g., keyboard, mouse, touch screen interface, displays, printers, speakers, audio inputs and outputs, video inputs and outputs, microphone jacks, etc.) to the computer 150, 160. A network interface 113 allows the computer to connect to various other devices attached to a network (for example the network illustrated at 170 of FIG. 1A). Memory 114 provides volatile storage for computer software instructions 115 and data 116 used to implement software implementations of the present invention (e.g. controllers 240, 340 and sensors 250, 350 of FIGS. 2 and 3).

Software components 115, 116 of the controlled environment system 100 (e.g. FIGS. 1A, 1B, 2 and 3) described herein may be configured using any programming language, including any high-level, object-oriented programming language.

The server may include instances of the controlled environment system 200 (FIG. 2) or 300 (FIG. 3), which can be implemented as a client 150 (e.g., sensors) that communicates to the server 160 (e.g., controller) utilizing various means, including encrypted data packets (e.g. via SSL), and may contain information regarding the gas concentrations or temperature of the shipping container. In addition, the system may include other instances of client processes executing on other client computers/devices 150, such as a client application that may communicate with the server (e.g., controller) to configure the parameters for releasing or shutting off release of gases from the stored compressed gas source. In some embodiments, the computing device 150 for configuring the parameters may be implemented via a software embodiment and may operate, at least partially, within a browser session.

In an example mobile implementation, a mobile agent implementation of the invention may be provided. A client server environment can be used to enable mobile configuration or monitoring of the sensors 150 or controller 160. It can use, for example, the XMPP protocol to tether a configuration server 115 on a device 150 to controller 160 or sensor 150. The server 160 can then issue commands via the mobile phone on request. The mobile user interface framework to access certain components of the system 100 may be based on XHP, Javelin and WURFL. In another example mobile implementation for OS X, iOS, and Android operating systems and their respective APIs, Cocoa and Cocoa Touch may be used to implement the client side components 115 using Objective-C or any other high-level programming language that adds Smalltalk-style messaging to the C programming language.

The system may also include instances of server processes on the server computers 160 that may comprise a controller 240 (FIG. 2) or 340 (FIG. 3), which allows monitor the sensors 250 (FIG. 2) or 350 (FIG. 3) of the controlled environment system to detect a low concentration of a particular gas, such as an ultra low oxygen concentration, or adjusting the sensors based on detected conditions of the controlled environment. The system may also include instances of server processes which release compressed gas into the interior of the container at various rates of release, and logs the gas concentrations or temperature in the controlled environment. In some embodiments, the server processes may comprise an industrial PLC, 240 (FIG. 2) or 340 (FIG. 3), or other such controller configured with firmware similar to PLC firmware.

Disk storage 117 provides non-volatile storage for computer software instructions 115 (equivalently "OS program") and data 116 used to implement embodiments of the system 100. The system may include disk storage accessible to the server computer 160. The server computer (e.g., controller) or client computer (e.g., sensors) may store information, such as logs, regarding the gas concentrations or temperature of the controlled environment. Central processor unit 112 is also attached to the system bus 110 and provides for the execution of computer instructions. Software implementations 115, 116 may be implemented as a computer readable medium capable of being stored on a storage device 117, which provides at least a portion of the software instructions for the controlled environment system. Executing instances of respective software components of the controlled environment system, may be implemented as computer program products 115 (e.g., PLC firmware), and can be installed by any suitable software installation procedure, as is well known in the art. In another embodiment, at least a portion of the system software instructions 115 may be downloaded over a cable, communication and/or wireless connection via, for example, a browser SSL session or through an app (whether executed from a mobile or other computing device). In other embodiments, the system 100 software components 115, may be implemented as a computer program propagated signal product embodied on a propagated signal on a propagation medium (e.g. a radio wave, an infrared wave, a laser wave, a sound wave, or an electrical wave propagated over a global network such as the Internet, or other networks. Such carrier medium or signal provides at least a portion of the software instructions for the present controlled environment system 100 of FIG. 1A.

Controlled Environment System

Improvements to the construction of refrigerated shipping containers are such that they are tightly sealed when closed and have limited permeability. After loading and sealing the container, the container will be flushed with an inert gas to remove oxygen and provide slight positive pressurization. The release of the stored compressed gas into the container, in the absence of a designated vent or other outlet, is expected to maintain slightly positive pressurization and to minimize infiltration of atmospheric gas into the container as required to maintain the environment within a desired range for key parameters.

The system and apparatus of the invention relies on the release of stored compressed gas which serves to (1) positively pressurize the container thereby minimizing the introduction of uncontrolled gases from the outside of the container, and (2) ensure more consistent concentrations of the composition of the mixture of gases due to the known high purity of the one or more stored compressed gases. In some embodiments, the system and apparatus may involve minimal additional equipment compatible with standard shipping containers. In addition, use of stored compressed gas may reduce the risk of product spoilage associated with mechanical failure of the more complex fuel cell or membrane based systems. Furthermore, the use of a stored compressed gas to maintain ultra low oxygen concentrations may provide the ability to release gas across a wider range of flow rates than can practically be achieved with fuel cell or membrane based systems. This may have value in the event of a sudden leak or influx of atmospheric gas from the exterior or interior of the container or from within product or packaging stored within said container.

In some embodiments, the system and apparatus of controlled environment containers may be used for transport or shipping perishable food products. The release of stored compressed gas may occur en route while the perishable food products are being shipped. In some embodiments, the system and apparatus of controlled environment containers may be used for storing perishable food products. The system and apparatus of controlled environment containers may be used for a time period of up to 100 days. For example, the time period for transport or shipping may be between 10 and 30 days.

In some embodiments, the spoilage of perishable food products may be due to oxidation or to decomposition by aerobic bacteria. In some embodiments, the perishable food products may be non-respiratory, i.e., do not take in oxygen with the corresponding release of carbon dioxide. For example, non-respiratory perishable food products include harvested fresh or processed fish, meat (such as beef, pork, and lamb), poultry (such as chicken, turkey, and duck), and bakery goods (such as bread, pastries, and grain-based snack foods).

In some embodiments, the system or apparatus has an ultra low oxygen concentration. For example, the oxygen concentration may be less than 6,000 ppm, less than 4,000 ppm, or less than 2,000 ppm.

In some embodiments, the system or apparatus for maintaining a low oxygen concentration comprises a container including a plurality of walls. The containers are sealed such that the containers can be operated with limited leakage of gases from the controlled environment containers. In some embodiments, the container may have limited oxygen permeability. In some embodiments, the container is a standard shipping container, and in other embodiments the container is a Controlled Atmosphere ("CA") shipping container. In some embodiments, the shipping container may be refrigerated to maintain freshness of perishable food products. For example, standard refrigerated shipping containers may be 10 feet, 20 feet or 40 feet in length and may be 8.5 feet or 9.5 feet high.

In some embodiments, the containers may be positively pressurized. For example, the pressure differential between the outside of the container and the inside of the container may be up to about 1 inch of water (0.002 atm).

In embodiments, standard refrigerated shipping containers may be outfitted with limited specialized equipment to monitor, control, and maintain an ultra low oxygen environment.

In embodiments, the composition of the mixture of gases includes one or more of nitrogen, carbon dioxide, and an inert gas. Carbon dioxide is colorless, odorless, noncombustible, and bacteriostatic, and it does not leave toxic residues on foods. Examples of inert gases include, but are not limited, to argon, krypton, helium, nitric oxide, nitrous oxide, and xenon. The composition of the mixture of gases can be varied as suitable for the perishable food products and is well within the knowledge and skill of the art. For example, the composition of the mixture of gases used for transport and storage of salmon is preferably 100% carbon dioxide. Other fish with lower fat content, such as cod or tilapia are preferably stored or shipped using 60% carbon dioxide and 40% nitrogen as the composition of the mixture of gases.

In embodiments, the system or apparatus includes at least one source of compressed or liquid nitrogen, carbon dioxide, and one or more inert gases to maintain the composition of the mixture of gases. The release of gas from a compressed source into the interior of the container may function to maintain a slight positive pressurization of the container's environment, which may be beneficial as it minimizes the rate at which atmospheric gases would enter the container and alter the composition or increase the oxygen level within the controlled environment. In some embodiments, the quantity of stored compressed gases is sufficient to maintain the container's environment at an ultra low oxygen concentration for the duration of the shipment. For example, the stored compressed gases occupy less than $\frac{1}{50}$ of the container volume, which will generally be sufficient to supply the quantity of inert gas needed to maintain the atmosphere within the desired range. In some embodiments, the system or apparatus further comprises a distribution system such as pipes to distribute the releases compressed gases.

In some embodiments, the source of compressed gas is within a rigid container, such as a gas cylinder, contained internally to the container. In some embodiments, compressed gas sources are maintained at a pressure of no greater than 6,000 psig and as low as 480 psig. In embodiments, a source of liquid gas may also be used, wherein the liquid gas container normally includes a means of vaporizing the liquid to release the gas at a working pressure of between 50 psig and 150 psig.

In embodiments, the system or apparatus includes one or more sensors that may provide traceability of key parameters of the container's environment. The sensors may be used to monitor the composition of the mixture of gases. The sensors may be used to monitor the gas concentrations and optionally maintain an electronic record of the gas concentrations. The sensors may be used to monitor the temperature of the container and optionally maintain an electronic record of the temperature of the container. The sensors may be used to monitor the rate of use of stored compressed gases and optionally maintain an electronic record of stored compressed gases.

In some embodiments, an oxygen sensor, for example, a trace oxygen sensor (Teledyne), is used to monitor the level of oxygen present in the container environment.

In some embodiments, the temperature control includes air conditioning or refrigeration. In preferred embodiments, the temperature control is part of the shipping container. Variation in the temperature is allowed as long as the temperature is maintained within a range to preserve the perishable food products. In some embodiments, the system or apparatus further comprises a sensor for monitoring and/or logging the temperature of the system or container. Such temperature sensors are commercially available from manufacturers including Sensitech, Temptale, Logtag, Dickson, Marathon, Testo, and Hobo. In some embodiments, the temperature sensor is part of the refrigerated shipping container. In some embodiments, the temperature sensor is an accessory that may be easily integrated into the system or apparatus of the invention.

In embodiments, the system or apparatus includes one or more controllers to release the compressed gases into the interior of the container, wherein a variable rate of release is sufficient to maintain the ultra low oxygen concentration and to ensure consistent concentrations of the mixture of gases within the container. In some embodiments, at least one controller may be an industrial PLC, or similar such industrial controller, and may be operated locally within the container. The controller may trigger release of gas(es) from a stored compressed gas source(s). The controller may, as an additional feature, use a proportional means of releasing the stored compressed gas such that the rate of release would be greater the further the gas concentration within the container was from the desired or set level. Additionally, the controllers may release the stored compressed gas at a rate which anticipates leakage or other sources of contribution of oxygen. In some embodiments, the controller may release the stored compressed gases at a rate designed to conserve the supply of compressed stored over the anticipated duration of the shipment. In some embodiments, the controller may be coupled to an oxygen sensor to minimize or shut off stored compressed gas release when the oxygen level is at or below a minimum set point. The controller may have value in the event of a sudden leak or influx of atmospheric gas from the exterior or interior of the container or from within product or packaging stored within said container.

In certain embodiments, the controller may use timed or programmed release of stored compressed gases. In embodiments, the controller may integrate predictive algorithms to regulate the rate of release of stored compressed gases. The predictive algorithms may be designed to maintain the ultra low oxygen concentration in the event of a sudden leak or influx of atmospheric gas from the exterior or interior of the container or from within product or packaging stored within said container.

In some embodiments, a power supply for the controller and sensors may be linked to the container. In some embodiments, a power supply for the controller and sensors may be independent of the container.

In some embodiments, the method of releasing stored compressed gas may rely on a standard or proportional solenoid valve. The stored compressed gas may be released into a distribution system to ensure uniform distribution within the container.

EXEMPLIFICATION

An example implementation of the apparatus or system 200 for maintaining ultra low oxygen concentration is depicted in FIG. 2. A shipping container 210 has the ambient atmosphere replaced with a composition of a mixture of gases 220, for example, one or more of nitrogen, carbon dioxide, and another inert gas. The shipping container also contains at least one source of compressed inert gas 230 with a controller 240, for example, a regulator with a shut off valve. There is also at least one sensor 250 to monitor the composition of gases, for example, the concentration of oxygen in the mixture of gases in the container. Optionally, additional sensors to monitor temperature, the gas mixture concentrations, and the rate of use of the stored gas may also be included. The schematic shows six cartons with perishable food products 260. The perishable food products may be packaged in other forms that are standard or accepted in the food product industry.

Figure 3:
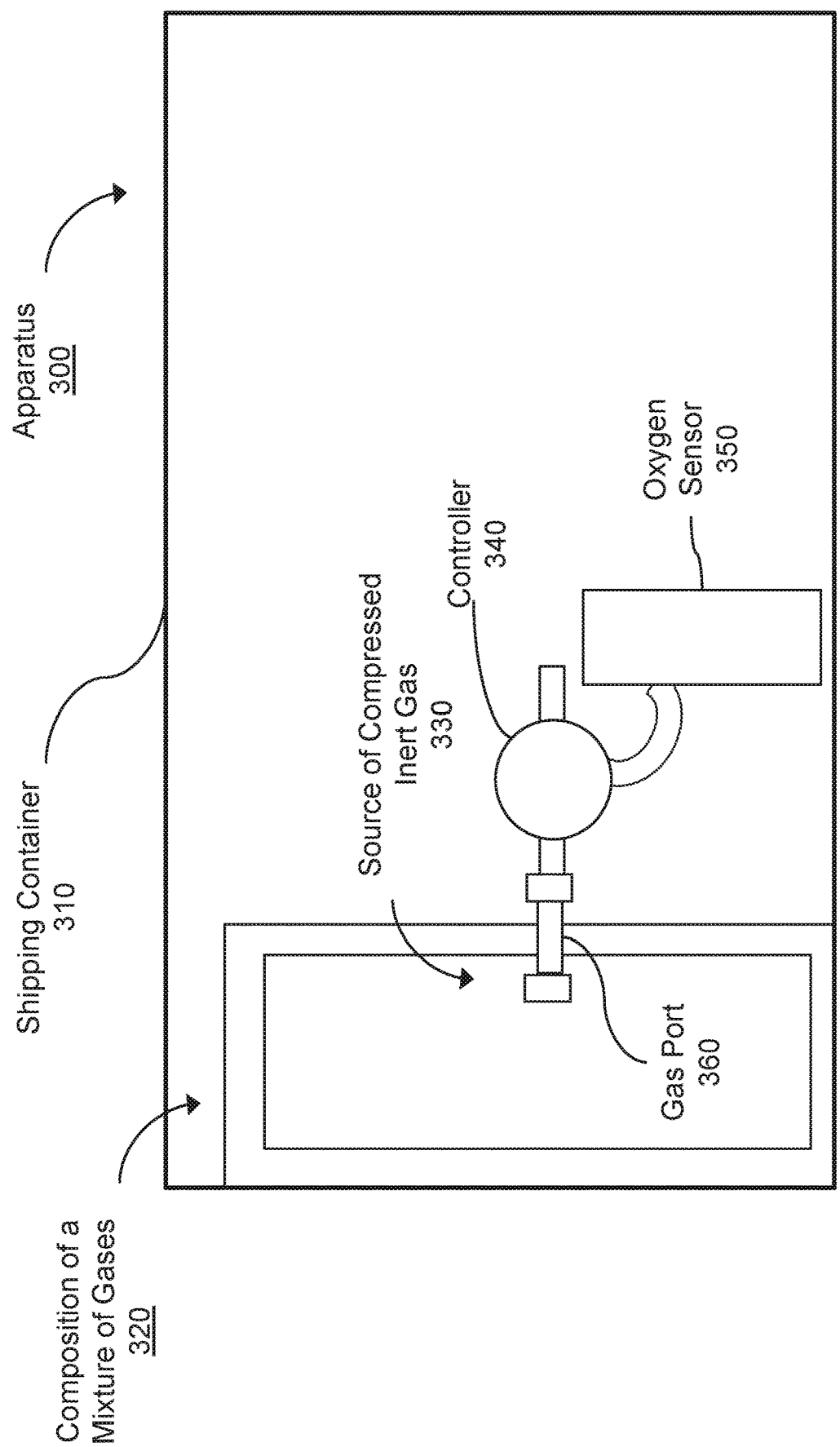
FIG. 3 shows a schematic of a system or apparatus in another embodiment focusing on a controller coupled to an oxygen sensor.

Another example implementation of the apparatus or system 300 for maintaining ultra low oxygen concentration is depicted in FIG. 3. A shipping container 310 has the ambient atmosphere replaced with a composition of a mixture of gases 320, for example, one or more of nitrogen, carbon dioxide, and another inert gas. The shipping container also contains at least one source of compressed inert gas 330, which may have an outlet or gas port 360 to the container atmosphere. The gas port 360 may be fitted with tubing with an optional valve. The gas port will be connected to a controller 340. In example embodiments, the controller is coupled to the oxygen sensor 350. Optionally, additional sensors to monitor temperature, the gas mixture concentrations, and the rate of use of the stored gas may also be included.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for maintaining an ultra low oxygen concentration to prevent spoilage of perishable food products, the apparatus comprising:
   at least one computing device, in communication with at least one electronic controllers, the at least one computing device arranged to:
   (i) execute predictive algorithms that regulate a release of at an inert compressed gas at a variable rate into an interior of a shipping container containing perishable products, such that the variable rate of the release maintains an ultra low oxygen concentration; and
   (ii) process input from one or more sensors coupled to the shipping container to monitor a composition of a mixture of gases in the shipping container, and to maintain an electronic record of at least one of: (a) temperature, (b) concentrations of the mixture of gases, or (c) rate of use of at least one of the mixture of gases.

2. The apparatus according to claim 1, wherein the container is a one of a standard shipping container or a Controlled Atmosphere ("CA") refrigerated shipping container having limited oxygen permeability.

3. The apparatus according to claim 1, wherein the mixture of gases positively pressurizes the container.

4. The apparatus according to claim 1, wherein the ultra low oxygen concentration is less than 6,000 ppm.

5. The apparatus according to claim 1, wherein one sensor of the one or more sensors monitors oxygen concentration.

6. The apparatus according to claim 1, wherein the at least one controller of is coupled to at least one of the one or more sensors to minimize or shut off the release when an oxygen level is at or below a minimum set point.

7. The apparatus according to claim 1, wherein a power supply is linked to the container.

8. The apparatus of claim 1, wherein the container comprises a gas cylinder, and wherein a regulator and shut off valve are coupled to the gas cylinder, the electronic controller being in electrical communication to control the regulator and shutoff valve.

9. The apparatus according to claim 1, wherein the predictive algorithms cause the ultra low oxygen concentration to be maintained in the event of at least one of: a sudden leak or influx of atmospheric gas from the exterior, or interior of the container, or from within product or packaging stored within said container.

10. A method of maintaining an ultra low oxygen concentration to prevent spoilage of perishable food products, the method comprising:
executing on a computing device, predictive algorithms that regulate a release of the inert compressed gas at a variable rate into an interior of a shipping container containing perishable products, such that the variable rate of the release maintains an ultra low oxygen concentration; and
computationally processing input from one or more sensors coupled to the shipping container to monitor a composition of a mixture of gases in the shipping container, and to maintain an electronic record of at least one of: (a) temperature, (b) concentrations of the mixture of gases, or (c) rate of use of at least one of the mixture of gases.

11. The method according to claim 10, wherein the container is a one of a standard shipping container or a Controlled Atmosphere ("CA") refrigerated shipping container having limited oxygen permeability.

12. The method according to claim 11, wherein the mixture of gases positively pressurizes the container.

13. The method according to claim 11, wherein the ultra low oxygen concentration is less than 6,000 ppm.

14. The method according to claim 11, wherein at least one of the one or more sensors monitors oxygen concentration.

15. The method according to claim 11, wherein one or more controllers is coupled to at least one of the one or more sensors sensor to minimize or shut off the release when an oxygen level is at or below a minimum set point.

16. The method according to claim 11, wherein a power supply is linked to the container.

17. The method of claim 11, wherein the container comprises a gas cylinder, and wherein a regulator and shut off valve are coupled to the gas cylinder, the electronic controller being in electrical communication to control the regulator and shutoff valve.

18. The method according to claim 11, wherein the predictive algorithms cause the ultra low oxygen concentration to be maintained in the event of at least one of: a sudden leak or influx of atmospheric gas from the exterior, or interior of the container, or from within product or packaging stored within said container.

19. A system comprising:
a mobile agent, executing on a computing device, in communication with an electronic controller that is configured to cause a release of inert compressed gas; and
the mobile agent, executing on the computing device, including:
(i) computationally processing predictive algorithms that regulate a release of the inert compressed gas at a variable rate into an interior of a shipping container containing perishable products, such that the variable rate of the release maintains an ultra low oxygen concentration; and
(ii) receiving input from one or more sensors coupled to the shipping container to monitor a composition of a mixture of gases in the shipping container, and to maintain an electronic record of at least one of: (a) temperature, (b) concentrations of the mixture of gases, or (c) rate of use of at least one of the mixture of gases.

20. The system as in claim 19 wherein the mobile agent is in communication with the electronic controller via a server computing system;
wherein the server computing system interfaces with the mobile agent to execute the predictive algorithms that regulate the release of the inert compressed gas at a variable rate into an interior of a shipping container;
the server causing using the predictive algorithms to cause the ultra low oxygen concentration to be maintained in the event of at least one of: a sudden leak or influx of atmospheric gas from the exterior, or interior of the container, or from within product or packaging stored within said container.

* * * * *

UNITED STATES PATENT AND TRADEMARK OFFICE
CERTIFICATE OF CORRECTION

PATENT NO.        : 11,064,709 B2
APPLICATION NO.   : 16/933602
DATED             : July 20, 2021
INVENTOR(S)       : Joshua N. Goldman Page 1 of 1

It is certified that error appears in the above-identified patent and that said Letters Patent is hereby corrected as shown below:

In the Claims

In Claim 15, Column 10, Line 6, delete "sensors sensor" and insert -- sensors --.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*